United States Patent
Nicolas et al.

(10) Patent No.: US 6,916,909 B1
(45) Date of Patent: Jul. 12, 2005

(54) COLLAGEN PEPTIDES MODIFIED BY GRAFTING MERCAPTO FUNCTIONS, METHOD FOR THE PRODUCTION THEREOF AND USES THEREOF AS BIOMATERIALS

(75) Inventors: Florence Nicolas, Genas (FR); Nathan Bryson, Millery (FR)

(73) Assignee: Flamel Technologies, Venissieux (FR)

( * ) Notice: Subject to any disclaimer, the term of this patent is extended or adjusted under 35 U.S.C. 154(b) by 0 days.

(21) Appl. No.: 09/914,426

(22) PCT Filed: Mar. 1, 2000

(86) PCT No.: PCT/FR00/00513

§ 371 (c)(1),
(2), (4) Date: Jan. 7, 2002

(87) PCT Pub. No.: WO00/52052

PCT Pub. Date: Sep. 8, 2000

(30) Foreign Application Priority Data

Mar. 2, 1999 (FR) .............................. 99 02727

(51) Int. Cl.[7] .......................... A61K 38/17; C07K 1/00; A61L 15/00; A61F 13/00
(52) U.S. Cl. ...................... 530/356; 530/402; 530/408; 530/410; 424/443; 424/444; 424/445; 424/484; 602/42; 602/43; 602/48; 602/50
(58) Field of Search ................................ 530/356, 402, 530/408, 410; 424/443, 444, 445, 484; 602/42, 43, 48, 50

(56) References Cited

U.S. PATENT DOCUMENTS

| | | | |
|---|---|---|---|
| 4,407,787 A | | 10/1983 | Stemberger .................. 424/28 |
| 5,412,076 A | * | 5/1995 | Gagnieu ...................... 530/356 |
| 5,763,579 A | * | 6/1998 | Gagnieu et al. ............ 530/356 |

FOREIGN PATENT DOCUMENTS

| | | |
|---|---|---|
| EP | 0 890 663 | 1/1999 |
| FR | 2 723 957 | 3/1996 |
| US | WO 90/05755 | 5/1990 |
| US | WO 94/01483 | 1/1994 |

OTHER PUBLICATIONS

Lin et al., Biochem. Biophys. Acta, vol. 1038, No. 3, pp. 382–385, 1990.*
Chemical abstract XP002125733, RN 60–23–1—Y. Chonan et al: Hikaku Kagaku, vol. 24, No. 3, 1978, pp. 140–147.
C. Lin et al: Biochim. Biophys. Acta, vol 1038, no 3, 1990, pp. 382–385, XP000864311.
Greene : Protecting Groups in Organic Chemistry, Wiley, 1975.
"Techniques in protein chemistry" R. L. Lundblad Chap. 10–14.
"Chemistry of protein conjugation and cross–linking" S. S. Wong, Boca raton, CRC Press, 1993, Chap. 2.

* cited by examiner

*Primary Examiner*—Jon Weber
*Assistant Examiner*—Abdel A. Mohamed
(74) *Attorney, Agent, or Firm*—Finnegan, Henderson, Farabow, Garrett & Dunner, L.L.P.

(57) ABSTRACT

The invention relates to novel collagen peptides that are modified by grafting free or substitued thiol functions carried by mercaptoamine radicals. The aim of the invention is to provide thiol collagens that can be cross-linked in a sufficient and controlled manner by forming S—S bridges and which are biocompatible. This is achieved by means of the inventive thiol collagens which are characterized in that the mercaptoamine radicals are identical to or different from each other and are exclusively grafted on the aspartic and glutamic acids of the collagen chain by amide bonds. The invention also relates to a method for the production of said thiol and cross-linkable collagens. The novel modified cross-linkable and/or cross-linked collagens can be used as biomaterials.

25 Claims, No Drawings

COLLAGEN PEPTIDES MODIFIED BY GRAFTING MERCAPTO FUNCTIONS, METHOD FOR THE PRODUCTION THEREOF AND USES THEREOF AS BIOMATERIALS

BACKGROUND OF THE INVENTION

The present invention relates to novel collagenic peptides chemically modified by grafting free or substituted thiol functions, borne by mercaptoamino residues. When the collagenic peptides comprise thiol functions, they have the property of being crosslinkable by oxidation and give a collagen derivative crosslinked with disulfide bridges.

The invention is also directed toward a process for preparing these novel collagen derivatives which are in crosslinkable form, in the form of a crosslinkable precursor of a derivative or in crosslinked form.

The invention also relates to the uses of these novel collagenic peptides as biomaterials that are useful as starting materials for the manufacture of medical, surgical or cosmetic products, such as artificial tissues or organs, artificial skin, bone, ligament, cardiovascular, intraocular, intraperitoneal, etc. prostheses or implants, or alternatively bioencapsulation systems (implants, microspheres or microcapsules) allowing the sustained and controlled release of active principles in vivo. Medical accessories such as suture threads and also biocompatibilizing coatings for implantable medical articles are other illustrations of the possible uses of the novel biomaterials according to the invention.

For the purposes of the present invention, the term "collagenic peptide" in particular denotes collagen with or without telopeptides, denatured collagen and also gelatin.

Various commercial grades of collagen, with or without telopeptides, are found on the market. These commercial collagens may be of human or animal origin. Collagen is a known protein, which is present at all the levels of organization of animal tissues: it is the main protein of the skin and of connective tissue. By nature, it has biochemical and physicochemical characteristics that are relatively well suited for uses as biomaterials. These characteristics are, in particular: good biocompatibility and biodegradability, hemostatic nature, etc.

However, it must be stated that collagen-based implantable medical, surgical or cosmetic articles suffer from certain shortcomings. They have poor mechanical characteristics, which makes them difficult to handle, or even makes them unusable for certain applications. Furthermore, their biodegradation may be too rapid when the implants need to exert palliative and/or curative functions for long periods. To improve the mechanical and biodegradation characteristics of collagen-based implants, it is found to be necessary to modify the collagen chemically, and in particular to crosslink it.

To modify, in particular to crosslink, collagenic peptides, the reactive functions present on the side chains of certain amino acids of collagen are used, namely:

the amine functions of the lysine residues, representing in numerical terms 3% of the amino acids,
the carboxylic acid functions of the aspartic acids and glutamic acids, representing in numerical terms 9% to 12% of the amino acids,
the alcohol functions of the serine, threonine and hydroxyproline residues, representing in numerical terms 14% of the amino acids.

Thus, four major technical types of artificial crosslinking of this collagenic peptide have appeared.
1. Creation of a network by covalent bonding between the collagen molecules, by irradiation or forced dehydration. This crosslinking is obtained without chemical functionalization of the collagen.
2. Activation of the natural groups of the collagen, to introduce the possibility of self-crosslinking, for example by oxidation (periodate) or by functional activation (activation of the acids with carbodiimides, in the form of azide . . . which react with the amines).
3. Crosslinking with difunctional or polyfunctional bridging chemical agents (aldehydes, dicarboxylic compounds, diamines, diisocyanates, disulfonyl chlorides or difunctionalized polyethylene glycol).
4. Copolymerization by covalent bonding of the collagen with another polymer (polyacrylic, copolyacrylo-nitrile-styrene, polyurethane, polyalcohol or silicone).

One crosslinking variant of type 3 by bridging may consist in using difunctional derivatives containing disulfide groups. This variant is the one which is of interest in the context of the invention. Said variant has given rise in the prior art to various technical propositions, which will be presented below.

The article by F. Schade & H. Zahn [Einbau von cystin-brücken in Kollagen, Angew. Chem., 74, 904, 1962], describes the functionalization of collagen using a cystine derivative, by formation of amide bonds between, on the one hand, the free $NH_2$ moieties of the lysine residues of the collagenic chain and, on the other hand, the carboxyl moieties of the cystine derivative, which have been preactivated by esterification with nitrophenol. The reduction of the disulfide bridges of the grafted cystine derivatives gives a thiolized material which is crosslinkable by oxidation. Since only the lysine residues of the collagen are functionalized, the maximum degree of functionalization, which is directly proportional to the level of crosslinking, is not more than 3% in numerical terms.

European patent application EP 0 049 469 discloses the functionalization of soluble collagen extracted from tendons using N-acetyl homocysteine thiolactone. This is also a case of a reaction between the carboxyl moieties of the functionalizing agent and the amine moieties of the lysine residues of the collagen. The maximum content of grafted thiol functions is thus in this case also not more than 3%.

In order to obtain novel thiolated collagenic derivatives and/or to increase the degrees of grafting of thiol functions on collagen and thereafter the level of crosslinking, the Applicant has proposed, in turn, three novel routes for chemical functionalization of collagen with groups bearing thiol functions or precursors thereof.

The first route is described in French patent FR 2 692 582 which concerns a collagen grafted with thiolated derivatives (cysteine, homocysteine or cysteamine):

via a succinic rotule, one of the carboxyl ends of which has reacted with amine moieties of the lysine residues and with certain alcohol moieties of the serine, threonine and hydroxyproline residues of the collagen and the other carboxyl end of which has reacted with the amine moiety of the thiolated derivative; and
optionally directly without a rotule on the carboxyl functions of the aspartic acids and glutamic acids of the collagen.

Up to 29% functionalization of the amino acids of the collagen may thus be achieved.

The mercaptoamino functions—that is to say the thiolated derivatives—described in said French patent are attached directly or indirectly to the free $NH_2$, OH and COOH functions of the collagen. Said patent does not disclose a collagenic peptide whose OH and $NH_2$ moieties are functionalized with functions other than mercaptoamino functions.

The second route is given in patent FR 2 699 184 which relates to a collagen grafted with thiolated derivatives (cysteine or homocysteine) attached directly to the amine moieties of the lysine residues and certain alcohol moieties of the serine, threonine and hydroxyproline residues. In accordance with the invention described by said patent, the functionalizing agent (e.g. cystine) which is the precursor of the thiolated derivative grafted onto the collagen comprises an activated carboxyl function, which reacts with the $NH_2$ functions of the lysines to form amides and with the OH functions of the serines, threonines and hydroxyprolines to form esters. This functionalizing agent also comprises a protected amine function, which cannot react with the carboxyls of the aspartic acids and glutamic acids of the collagenic chain. The maximum degree of grafting which may be achieved by this method is 17%.

A third route for the chemical modification of collagen which was developed by the Applicant to provide such a polymer with crosslinking functionality, is described in French patent FR 2 723 957. Said patent discloses a collagen grafted on the free amine moieties of its lysine residues with a thiolated derivative consisting of cysteine or homocysteine whose amine and thiol functions are protected with one and the same protecting group, the whole forming a thiazolidine moiety. The carboxylic acid of the thiazolidine derivative is activated to be able to react with the amine functions of the lysine residues. Consequently, the degree of grafting in this case is not more than 3%. The free carboxylic functions of the glutamic acids and aspartic acids of the collagenic chain are not substituted in the collagen according to said patent.

The collagens according to these three French patents allow the preparation of medical articles (gels, felts, films, etc.) with advantageous levels of crosslinking, that is to say advantageous mechanical and biodegradation characteristics. However, there is scope for their improvement.

Collagens substituted with groups which are not crosslinking functions and which are intended to give the collagen other properties, for example by modifying its solubility characteristics and/or its rheological characteristics and/or its biological characteristics, are moreover known. Thus, patent application PCT WO 90/05755 describes a collagen in which the amines of the lysine residues it comprises are substituted with a synthetic hydrophilic polymer chain and more particularly with monomethyl polyethylene glycol. This collagen-PEG is presented as having low immunogenicity and improved mechanical properties of elasticity and malleability.

Patent application PCT WO 94/01483 discloses a biologically inert, biocompatible conjugated polymer material, formed by a natural polymer such as collagen, linked via an ether bond to a synthetic hydrophilic polymer such as polyethylene glycol (PEG).

The modified collagens according to the prior art do not afford all the desired satisfaction, as regards their mechanical properties, their in vivo degradation kinetics and their biological characteristics. Moreover, the known collagens modified with free or substituted thiol functions still have scope for improvement, as regards controlling, by means of the degree of crosslinking, their mechanical and biological characteristics.

Finally, it would be advantageous for the crosslinkable forms of the known modified collagens to have solubility properties over a wide pH range, so as to make them easier to use, without this having a negative effect on their level of crosslinking.

In this prior art, one of the essential objectives of the invention is to provide novel collagens modified by grafting free or substituted thiol functions, these novel collagens needing to be capable of crosslinking in a sufficient and controlled manner, by forming intercatenary disulfide bridges.

Another essential objective of the invention is to provide novel collagens modified by grafting thiol functions and characterized by high degrees of grafting coexisting with good solubility over a wide pH range.

Another essential objective of the invention is to provide novel collagens modified by grafting thiol functions, that are easy to use and to handle industrially.

Another essential objective of the invention is to provide novel collagens modified by grafting thiol functions, in which the reactive functions are not all mobilized by crosslinking, so as to allow the grafting of noncrosslinking functionalities.

Another essential objective of the invention is to provide novel crosslinkable collagens or crosslinkable collagen precursors that are mercapto-functionalized and able to be converted into gels, films or felts (e.g.) whose crosslinking density (and thus mechanical strength and biodegradation) may be modified beforehand, so as to provide a varied range of starting materials which may be used in numerous applications as biomaterials.

Another essential objective of the invention is to provide a simple process for preparing a collagenic peptide modified by grafting free or substituted thiol functions borne by mercaptoamino residues.

BRIEF SUMMARY OF THE INVENTION

The inventors have, to their credit, achieved all these objectives, among others, by revealing the fact that the carboxylic functions of the aspartic acids and glutamic acids of the collagenic chain should be favored, as sites for grafting mercaptoamino functions which are the source of the crosslinking properties by S—S bridging between the collagenic chains.

Thus, the present invention relates, firstly, to a collagenic peptide modified by grafting free or substituted thiol functions, borne by mercaptamino residues, characterized in that these mercaptoamino residues are identical to or different than each other and are exclusively grafted onto the aspartic acids and glutamic acids of the collagenic chain via amide bonds, and in that said modified collagenic peptide is soluble in aqueous medium and/or in polar solvents.

The fact that the crosslinking functionalities are borne by the carboxylic residues of the aspartic acids and glutamic acids gives the collagenic peptide according to the invention advantageous properties that are entirely unexpected in mechanical and biological terms. Specifically, this modified collagenic peptide can, since it is in reduced thiol form, be crosslinked in a controlled manner, achieving degrees of crosslinking which afford it stability and also good mechanical properties and modifiable biodegradability. Furthermore, since the lysine residues are not involved in the grafting of the mercaptoamino residues, they may serve as sites of attachment for other groups and may afford the product diverse and varied functionalities that are useful in the intended applications.

When the collagenic peptide corresponds to native collagen with or without telopeptide, the degree of functionalization with mercaptoamino residues may reach 9% to 12% in numerical terms, since this corresponds to the ratio of amino acids of aspartic acid or glutamic acid type constituting the collagen. Asparagines and glutamines whose amides are capable of being hydrolyzed to form the corresponding acid derivatives are compatibilized in this ratio.

According to one advantageous characteristic of the invention, this high degree of grafting is not incompatible with high solubility of the crosslinkable (non-crosslinked) forms of the modified collagen, in aqueous medium and/or in polar solvents and over a wide pH range. This makes it very easy to use.

DETAILED DESCRIPTION OF THE INVENTION

In order to be able to crosslink by disulfide bridging, the modified mercaptoamino functionalities according to the invention need to be in reduced form, that is to say in thiol form (—SH). It is thus when they are in this form that the modified collagenic peptides may be termed "crosslinkable". This term reflects the ability of the modified collagenic peptides to self-crosslink spontaneously in the presence of atmospheric oxygen, at ambient temperature and optionally in the presence of auxiliary agents such as oxidizing agents.

The mercaptoamino residues bearing crosslinking functions of free thiol type or precursors thereof in substituted thiol form are advantageously residues that are closely or remotely derived from cysteine or analogues thereof: cysteamine and homocysteine. It is interesting to note that these various mercaptoamino residues are of biological nature.

In the present specification, two types of monovalent mercaptoamino residues or grafts are distinguished, namely those bearing directly crosslinkable thiol functions and those bearing mercapto functions that are precursors of said thiol functions.

As regards the mercaptans that are thiol precursors, they define a first subfamily of modified collagenic peptides according to the invention characterized in that at least some of the mercaptoamino residues, grafted onto the carboxylic acids of the aspartic acids and glutamic acids, correspond to the general formula (I) below:

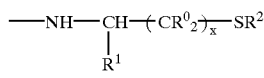
(I)

in which x=1 or 2;

$R^0$=H or $CH_3$;

$R^1$ represents H or $COOR^3$ with $R^3$ corresponding to a hydrocarbon-based radical of aliphatic, aromatic or alicyclic type, preferably alkyl, alkenyl, aryl, aralkyl, alkylaryl, aralkenyl or alkenylaryl type and even more preferably of methyl or ethyl type;

$R^2$ is an aliphatic and/or alicyclic and/or aromatic radical, preferably an alkyl or an acyl optionally containing sulfur and/or amino, and even more preferably $R^2$ corresponds to formula (II) below:

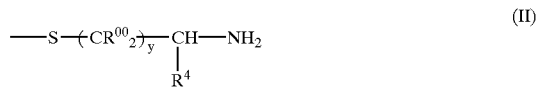
(II)

with y, $R^{00}$ and $R^4$ corresponding to the same definition as that given in the legend in formula (I) for x, $R^0$ and $R^1$.

More specifically, the grafted mercaptoamino residues of these collagenic peptides, that are not immediately crosslinkable, are chosen from the group of monovalent radicals comprising:

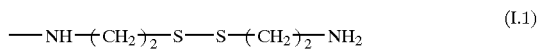
(I.1)

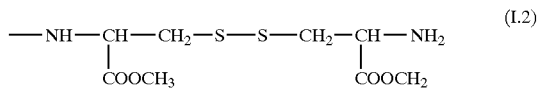
(I.2)

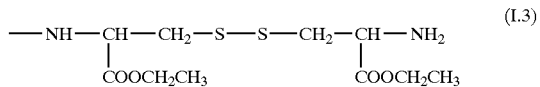
(I.3)

These are grafts derived from cystine and thus comprising a disulfide bridge which may be reduced with known reducing agents such as mercaptans (mercaptoethanol, mercaptoacetic acid, mercaptoethylamine, benzyl mercaptan, thioresol, dithiothreitol, etc.) and/or reductive salts ($NaBH_4$, $Na_2SO_8$, etc.) and/or organic reducing agents (phosphine).

These novel modified collagenic intermediates according to this first subfamily are stable and soluble in water and more generally in aqueous medium and/or in polar solvents. In addition, they are readily purifiable and isolable, which makes them products that are practical for packaging, storage and use.

The second subfamily of modified collagenic peptides according to the invention combines those in which the carboxyls of the glutamic acids and aspartic acids have reacted with the amine functions of the mercaptoamino residues of formula (I) in which the substituent $R^2$ corresponds to hydrogen.

The modified collagenic peptides according to the second subfamily may be prepared by reducing the collagenic peptides according to the first subfamily, using reducing agents such as those defined above.

These reduced collagenic peptides are readily purifiable and isolable. Since they are obtained in dry form after an isolation in acidic medium, these peptides are stable. Finally, they are soluble in water and more generally in aqueous medium and/or in polar solvents and are easy to use.

The mercaptoamino residues of these peptides containing free thiol functions are defined by formula (II) below:

(I')

in which $R^1$ may correspond to H or $COOR^3$, with x, $R^1$, $R^0$ and $R^3$ as defined above, and also $R^3$ may represent hydrogen or a cation to form a salt with $COO^-$, this cation preferably being $Na^+$, $K^+$ or $Li^+$, when a step of deprotection of the ester is provided. The graft thus used is derived directly from cysteine.

Collagenic peptides comprising such mercaptoamino residues containing thiol reactive functions have the characteristic of being crosslinkable within the meaning of the invention.

The crosslinking is carried out by oxidizing the thiols to disulfide bridges, which makes it possible to obtain a chemically crosslinked three-dimensional collagenic network, which is insoluble in physiological media and entirely stable. This oxidation may be obtained, for example, with atmospheric oxygen in weakly basic medium, with aqueous hydrogen peroxide solution or with iodo derivatives (iodine, betadine).

Among the modified collagenic peptides in accordance with the invention, it is possible to isolate those which exist in crosslinked form and which compose a third subfamily of collagenic peptides comprising collagenic chains linked together via disulfide bridges, in which the constituent sulfur atoms belong to mercaptoamino residues grafted onto the aspartic acids and glutamic acids of the collagenic chains, exclusively via amide bonds.

These crosslinked collagenic peptides of the third subfamily may be advantageously obtained from the modified collagenic peptides of the second subfamily.

These crosslinked collagenic peptides are novel, stable products whose mechanical and biological qualities make them biomaterials of choice for producing medical or surgical articles such as implants, prostheses, dressings or artificial skin. Since it is possible to vary the degree of substitution of the carboxylic moieties of the aspartic acids and glutamic acids, there is certain room for maneuver in choosing the appropriate mechanical quality and the appropriate rate of biodegradation.

Moreover, the crosslinked form which is of concern for these collagenic peptides belonging to the third subfamily described in the present specification, is reversible. Specifically, it is possible to reduce the disulfide bridges using suitable reducing agents. Examples of these reducing agents are given above.

In accordance with the invention, the free carboxylic residues of the aspartic acid and glutamic acid monomers of the collagenic chain are mobilized for the grafting of crosslinking functionalities. However, the fact nevertheless remains that at least some of the other free functions of the collagenic chain, such as, for example, the amine functions lysine residues, may serve as sites of attachment for groups other than the mercaptoamino residues as defined above and which afford diverse and varied functionalities, that are useful in the intended applications.

As a result, the collagenic peptides as defined above may comprise, according to one variant, grafts G attached to at least some of the free amine moieties of the collagenic chain, via amide bonds, G being an acyl comprising a hydrocarbon-based species, WITH THE EXCLUSION of the mercaptoamino residues, in particular those as defined above, this species optionally comprising hetero atoms (advantageously O and/or N) and preferably being chosen from alkyls and/or alkenyls and/or alicyclics and/or aromatics and even more preferably from groups comprising an optionally unsaturated alkyl chain, containing from 1 to 22 carbon(s) or corresponding to the formula (III) below:

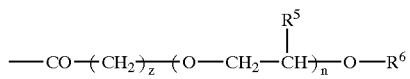

(III)

with $R^5$=H or $CH_3$;

$R^6$=H or a linear or branched alkyl radical and preferably a methyl;

z=0, 1 or 2 and n>0.

The number of repeating units n is chosen such that the molecular weight of the polymer chain is between 100 and 15000, preferably between 200 and 8000, and is, for example, about 4000.

This additional functionalization on the amine sites of the lysines may give the modified collagenic peptide a hydrophilic or hydrophobic nature, or even a surfactant nature, which allows the swelling, mechanical strength and degradation kinetics properties to be modified. It is also conceivable for this functionalization to have therapeutic aims by means of the attachment of an active principle.

In addition to the collagenic product aspect taken as such, the present invention also relates to the production of modified collagenic peptides, and in particular those as defined above and even more particularly those belonging to the three subfamilies presented above.

The invention thus relates to a process for obtaining a collagenic peptide modified by grafting free or substituted thiol functions borne by mercaptoamino residues. This process consists essentially in reacting the collagenic peptide in solution with at least one precursor of a mercaptoamino residue in which the thiol function and the possible carboxylic function are blocked, in the presence of at least one grafting agent preferably chosen from the group of products for activating carboxylic groups and even more preferably from carbodiimides.

The production conditions are chosen such that the grafting of the mercaptoamino residue is carried out on the free carboxylic moieties of the aspartic acids and glutamic acids of the collagenic chain.

This process is particularly novel and advantageous in that it can be performed in aqueous medium in which the starting materials and/or the intermediate products and/or the final modified collagens are at least partially dissolved.

In practice, all the products contained in the aqueous reaction medium are dissolved therein, from the first to the last step.

This synthesis in aqueous medium, in accordance with the invention, is particularly advantageous industrially, since it is very simple to carry out, inexpensive and nonpolluting. Specifically, it is easy, for example, to remove the reagents (e.g. by diafiltration) and to recover the targeted modified collagen.

The process according to the invention is all the more advantageous since it makes it possible to achieve high degrees of grafting of mercaptoamino residues (e.g. 12%). Preferably, the mercaptoamino residues (monovalent groups) which are grafted onto the collagenic peptide are those as defined above, in particular in formulae (I), (I.1), (I.2) and (I.3).

In practice, the collagenic peptides thus obtained correspond, for example, to the precursors as targeted above, of crosslinkable collagenic peptides. These precursors are included in the first subfamily of modified collagenic peptides according to the invention.

In order to be able to react with the free carboxylic moieties of the collagenic peptide, the mercaptoamino graft has a free amine function capable of reacting with the COOHs to form an amide bond. This precursor is, for example, a cysteine, a homocysteine or a cysteamine in which the thiol function and the possible carboxylic acid function is (are) correctly protected. An efficient means for protecting the thiol function is to choose as precursor for the mercaptoamino residue to be grafted, cystine, homocystine or cystamine, which comprise a disulfide bridge that stabilizes the mercapto function. Another means for protecting said function which may be chosen is any conventional function for protecting thiols that is known in the prior art (see, for example, "Greene: *Protecting Groups in Organic Chemistry*, Wiley, 1975").

The possible COOH functions of the graft may themselves be protected with a protecting group or any other organic function which may provide an advantageous property of any nature (PEGs or hydrophobic or hydrophilic or charged groups).

According to one advantageous arrangement of the invention, the precursor of the mercaptoamino residue corresponds to a formula (IV) corresponding to formula (I) given above and in which the free valency is replaced with a substituent capable of reacting with the carboxylic functions of the aspartic acids and glutamic acids of the collagenic chain, this substituent preferably being hydrogen, such that the reactive function is a primary amine. The precursors of formula (IV) that are most especially preferred are cystamine (I.1), cystine dimethyl ester (I.2) and cystine diethyl ester (I.3), all three of which comprise a disulfide bridge that protects the thiol function.

In practice, the grafting of the-mercaptoamino residue is carried out by dissolving the collagenic peptide and then the precursor of the mercaptoamino residue to be grafted in a suitable solvent. This solvent may be, for example, water (preferably) and/or an organic solvent, for instance dimethyl sulfoxide (DMSO), N-methylpyrrolidone (NMP) or the like.

The reaction conditions are chosen so as to prevent the activated collagen from reacting with the amines contained in its own skeleton.

A coupling agent, such as a carbodiimide, is then added to the reaction solution and the grafting is left to proceed while stirring the medium for a few hours, at ambient temperature.

The process according to the invention makes it possible to obtain collagenic peptides substituted with mercaptoamino residues that are precursors of the crosslinkable thiol residues. The peptides thus obtained are novel intermediate products that are stable and soluble in water. They may be isolated and purified, for example by dialysis or diafiltration and then lyophilization or by precipitation in organic medium and then drying.

A subject of the present invention is also a process for preparing a crosslinkable collagenic peptide modified by grafting free thiol functions borne by mercaptoamino residues. This process is characterized in that it consists essentially:
1. in reacting in solution the collagenic peptide with at least one precursor of a mercaptoamino residue whose thiol function and possible carboxylic function are blocked, in the presence of at least one grafting agent preferably chosen from the group comprising products that activate carboxylic groups, preferably carbodiimides,
2. and in deprotecting (conversion to thiols) the mercapto functions of the mercaptoamino residues grafted onto the modified collagenic peptides obtained in step 1.

The crosslinkable collagenic peptides thus prepared correspond, for example to the products containing free thiol functions included in the second subfamily of modified collagenic peptides, as defined above.

When the protection or masking of the mercapto functions is provided by a disulfide bridge (that is to say when the graft precursors are, for example, cystamine or cystine), the thiol function is regenerated by reduction.

This reduction may be carried out using reducing agents such as mercaptans (mercaptoethanol, mercaptoacetic acid, mercaptoethylamine, benzyl mercaptan, thiocresol, dithiothreitol, etc.) and/or reductive salts ($NaBH_4$, $Na_2SO_3$, etc.) and/or organic reducing agents (phosphine).

According to one preferred characteristic of the present invention, the protective disulfide bridge is reduced in basic aqueous medium using dithiothreitol. After this step, the thiolated collagen obtained is purified by dialysis/diafiltration and may be isolated, for example by lyophilization.

The invention also relates to a process for preparing a crosslinked collagenic peptide, from a collagenic peptide modified by grafting free thiol functions borne by mercaptoamino residues. This process is characterized in that it consists, essentially:
1. in reacting in solution the collagenic peptide with at least one precursor of a mercaptoamino residue whose thiol function and possible carboxylic function are blocked, in the presence of at least one grafting agent preferably chosen from the group comprising products that activate carboxylic groups, preferably carbodiimides,
2. and in deprotecting (conversion to thiols) the mercapto functions of the mercaptoamino residues grafted onto the modified collagenic peptides obtained in step 1,
3. and in oxidizing the thiol functions of the crosslinkable modified collagenic peptide obtained in step 2, so as to form intercatenary disulfide bridges.

This oxidation may be carried out, for example, using atmospheric oxygen in weakly basic medium, or using aqueous hydrogen peroxide solution or iodo derivatives (iodine, betadine).

The crosslinked collagenic peptides, as prepared by the above process, correspond in particular to the crosslinked products of the third subfamily of modified collagenic peptides as defined above.

According to one advantageous characteristic which is intrinsic to the three processes described above, an additional step F is envisaged, this being a step of functionalization with grafts G that are different in nature from the grafts attached to the carboxylic functions of the aspartic acids and glutamic acids, this step F consisting essentially in carrying out an acylation of at least some of the free amine functions of the collagenic chain, so as to attach thereto grafts G comprising a hydrocarbon-based species, WITH THE EXCLUSION of mercaptoamino residues, in particular those as defined above, this species optionally comprising hetero atoms (advantageously O and/or N) and preferably being chosen from alkyls and/or alkenyls and/or alicyclics and/or aromatics, and even more preferably from groups comprising an optionally unsaturated alkyl chain or corresponding to formula (III) below:

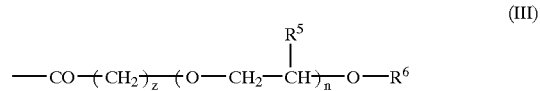

(III)

with
R=H or $CH_3$;
$R^6$=H or a linear or branched alkyl radical and preferably a methyl;
z=0, 1 or 2 and n>0.

In order to be able to react by acylation with the three amine functions of the residue of the collagenic chain, the precursors of the grafts G advantageously comprise at least one activatable carboxylic acid function.

It is preferable for this acylation to proceed before the reaction of the free carboxylic functions of the collagenic chain with the precursor of the mercaptoamino graft (I). Having said this, it is not excluded for this acylation also to take place on the thiolated collagenic peptides obtained from step 1 and/or on the crosslinked collagenic peptides obtained from step 3 (e.g. directly on a crosslinked film, with removal of the reagents by simple washing).

The acylation and coupling reactions of amine functions with carboxylic sites belonging to proteins are known to those skilled in the field of protein biochemistry. For further details in this respect, reference will be made in particular to the following books:

"*Techniques in protein chemistry*" R. L. Lundblad Chap. 10–14.

"*Chemistry of protein conjugation and cross-linking*" S. S. Wong, Boca raton, CRC Press, 1993, Chap. 2.

It is interesting to note that the reagents used for the chemical modifications performed according to the processes in accordance with the invention are either convertible into nontoxic products or readily removable by nondegrading processes such as, for example, dialysis.

Moreover, the invention offers the very appreciable possibility of controlling the kinetics and the degree of crosslinking of the collagen.

Another appreciable advantage of the present invention is that it allows the mechanical and biodegradation properties to be modified by controlling the number of mercaptoamino residues introduced per unit of mass of the collagen.

It is also interesting to be able to functionalize the crosslinked or noncrosslinked collagenic chains with hydrophilic functions, for example.

Finally, it is important to point out that the products according to the invention may be sterilized by the conventional methods for sterilizing biological polymers.

Finally, the very good solubility of the novel noncrosslinked collagenic peptides according to the invention in aqueous medium must be stressed, these peptides having the characteristic of containing sulfur-containing crosslinking functions borne exclusively by the carboxyls of the aspartic acids and glutamic acids.

As a result, the crosslinkable products according to the invention find immediate applications firstly in human medicine and secondly in the field of biology.

In human medicine, they may implants, for ophthalmological implants, prostheses (for example bone prostheses), dressings in the form of films or felts, artificial tissues (epidermis, blood vessels, ligaments or bone), bioencapsulation systems (microspheres or microcapsules) allowing the controlled release of active principles in vivo, biocompatibilizing coatings for implantable medical articles, or suture threads. The crosslinkable collagenic products according to the invention may also be used in surgery, as adhesives and/or as sealing materials (cements).

In biology, the materials according to the invention constitute excellent supports for two-dimensional cell cultures (films) and three-dimensional cell cultures (felts).

The crosslinked collagen according to the invention may be used alone or as a mixture, for example with modified or unmodified biological polymers or synthetic polymers.

For each of the abovementioned biomedical applications, it is essential to have available a crosslinked collagen which has determined and specific physicochemical, mechanical or biological properties. Consequently, it is necessary to control fully the chemical modifications of the collagen, so as to be able to produce a wide range of crosslinkable collagens and thus to satisfy most of the constraints appearing during the development of the specifications for a given application. It emerges from the above description that the invention fully satisfies this need.

Other advantages and variants of the present invention will emerge clearly from the implementation examples given below.

EXAMPLES

Example 1

Synthesis of a Collagenic Peptide (2nd Subfamily) in which the Carboxylic Acids are Substituted with Cysteine Ethyl Ester (Degree of Substitution Representing 0.8% of the Amino Acids)

1) Step I: Coupling (Production of 1st Subfamily):

25 g of atelocollagen (types I+III, extracted from calf skins, 1.3 mmol of COOH/g) are placed in 2.5 l of water and the temperature of the medium is raised to 50° C. with stirring. The 1% w/v solution thus obtained is filtered through a 0.22 µm filter.

Once the temperature has fallen to 30° C., 46.5 g of cystine diethyl ester are added and the pH is adjusted to 4.2. 0.6 g of 1-(3-dimethylaminopropyl)-3-ethylcarbodiimide HCl is then added and the reaction is left to proceed for 2 h at 30° C. with stirring. The reaction medium is concentrated to 5% w/v and dialyzed against water to remove the excess reagents and the reaction byproducts.

The product obtained is a stable synthetic intermediate. It is a collagenic peptide (1st subfamily) a fraction of the aspartic acids and glutamic acids of which are substituted with cystine diethyl ester.

The degree of substitution is measured by assaying with NSTB (2-nitro-5-thiosulfobenzoate), a reagent for disulfide bridges. This assay is described in: Thannhauser T. W. et al., Analysis of disulfide bonds in peptides and proteins. *Methods in Enzymology*. Jacoby W. B. and Griffith O. XL New-York: Academic Press, 1987. Vol. 143, 115–119.

[S—S]: 0.094 mmol/g of dry product; i.e. 0.87 mol % of substituted amino acids.

The product obtained may be isolated by lyophilization or may be reduced to give the corresponding thiol collagen.

2) Step II: Reduction (Production of 2nd Subfamily):

7.6 g of glycine, 5.8 g of 1,4-dithiothreitol and a sufficient amount of 4N NaOH to reach a pH of 9.0 are added to the modified collagenic peptide dissolved at 5% w/v in water, obtained in step I. The reaction medium is stirred for three hours at 35° C. At this stage, the solution is acidified to pH 2 with 6N HCl, dialyzed against 0.012N HCl to remove all trace of reagents and of reaction byproducts and then filtered through a 0.22 µm filter. The product thus purified is isolated by lyophilization.

The degree of substitution is measured by an assay with 5,5'-dithiobis-2-nitrobenzoic acid (DTNB), a reagent which is specific for thiol functions. This assay is described in: "Ellman G. L., Tissue sulfhydryl groups, *Archives of Biochemistry and Biophysics*, 1959, 82, 70–77".

[SH]: 0.091 mmol/g of dry product, i.e. 0.8 mol % of substituted amino acids.

The entire synthesis may be performed aseptically so as to obtain in fine the product in the form of a sterile lyophilizate.

Example 2

Synthesis of a Collagenic Peptide (2nd Subfamily) in which the Carboxylic Acids are Substituted with Cysteine Ethyl Ester (Degree of Substitution Representing 3 Mol % of the amino Acids)

Example 1 is repeated, the only difference being that the amount of coupling agent is 2.9 g.

[SH]: 0.347 mmol/g of dry product, i.e. 3.3 mol % of substituted amino acids.

Example 3

Synthesis of a Collagenic Peptide (2nd Subfamily) in which the Carboxylic Acids are Substituted with Cysteine Ethyl Ester (Degree of Substitution Representing 7 Mol % of the Amino Acids)

Example 1 is repeated, the only difference being that the amount of coupling agent is 12 g.

[SH]: 0.706 mmol/g of dry product, i.e. 7 mol % of substituted amino acids.

Example 4

Synthesis of a Gelatin (2nd Subfamily) in which the Carboxylic Acids are Substituted with Cysteine Ethyl Ester (Degree of Substitution Representing 5 Mol % of the Amino Acids)

Example 1 is repeated, replacing the atelocollagen with gelatin (gelatin extracted from pig skins, 250 bloom, 1 mmol of COOH/g).

[SH]: 0.536 mmol/g of dry product, i.e. 5.2 mol % of substituted amino acids.

Example 5

Synthesis of a Collagenic Peptide (2nd Subfamily) in which the Carboxylic Acids are Substituted with Cysteamine (Degree of Substitution Representing 3 Mol % of the Amino Acids)

Example 1 is repeated, replacing 46.5 g of cystine diethyl ester with 28.4 of cystamine.

[SH]: 0.33 mmol/g of dry product, i.e. 3.0 mol % of substituted amino acids.

Example 6

Synthesis of a Collagenic Peptide (2nd Subfamily) in which the Amines are Acetylated (Graft G) and in which the Carboxylic Acids are Substituted with Cysteine Ethyl Ester (Degree of Substitution Representing 5 Mol % of the Amino Acids)

25 g of atelocollagen (types I+III, extracted from calf skins, 1.0 mmol of COOH/g; 0.33 mol of $\epsilon$-$NH_2$/g) are placed in 0.5 l of water and the temperature of the medium is raised to 50° C. with stirring. The 5% w/v solution thus obtained is filtered through a 0.22 μm filter.

After cooling the solution to 30° C., 4.2 g of $NaHCO_3$ and a sufficient quantity of 4N NaOH to adjust the pH to 8.5 are dissolved. 7.34 ml of acetic anhydride are then added slowly and sequentially, over 30 minutes with stirring at 30° C., while maintaining the pH at 8.5 with 4N sodium hydroxide solution. The solution is then acidified slowly to pH 3 with 6N HCl and is dialyzed against water to remove the excess reagents. Finally, the 1% w/v medium is diluted with water and the synthesis is continued as described in Example 1 (coupling of cystine diethyl ester followed by reduction).

[acetyl] by assay of acetic acid (Boehringer kit) after basic hydrolysis of the product: 0.30 mmol/g of dry product, i.e. 2.9 mol % of acetylated amino acids (virtually total acetylation of the lysine residues).

[SH]: 0.53 mmol/g of product, i.e. 5.1 mol % of substituted amino acids.

Example 7

Synthesis of a Collagenic Peptide (2nd Subfamily) in which the Amines are Substituted with PEG (Graft G) and in which the Carboxylic Acids are Substituted with Cysteine Ethyl Ester (Degree of Substitution Representing 5 Mol % of the Amino Acids)

10 g of atelocollagen (types I+III, extracted from calf skins, 1.3 mmol of COOH/g; 0.33 mol of $\epsilon$-$NH_2$/g) are placed in 0.5 l of water and the temperature of the medium is raised to 50° C. with stirring. The 2% w/v solution thus obtained is filtered through a 0.22 μm filter. Once the temperature has fallen to 30° C., the pH is adjusted to 9.0 with 4N NaOH. 5 g of methoxypolyethylene glycol propionic acid N-hydroxysuccinimidyl ester (SPA-PEG) of MW 5000 g/mol are then added and the reaction is left to proceed at 30° C. with stirring for 30 min, while maintaining the pH at 9 by adding 4N NaOH. A further 5 g of SPA-PEG are added and the reaction medium is stirred for 30 min while maintaining the pH. The medium is then diluted to ½ with water to bring the collagen concentration to 1% w/v.

18.5 g of cystine diethyl ester are added and the pH is adjusted to 4.2. 2.2 g of 1-(3-dimethylaminopropyl)-3-ethylcarbodiimide HCL are then added and the reaction is left to proceed for 2 h at 30° C. with stirring. The reaction medium is concentrated to 5% w/v and dialyzed against water to remove the excess reagents and the reaction byproducts.

3.0 g of glycine, 2.3 g of 1,4-dithiothreitol and a sufficient quantity of 4N NaOH to reach a pH of 9.0 are added to the modified collagenic peptide dissolved at 5% w/v in water. The reaction medium is stirred for 3 hours at 35° C. At this stage, the solution is acidified to pH 2 with 6N HCl, dialyzed against 0.012 N HCl to remove all trace of reagents and reaction byproducts and then filtered through a 0.22 μm filter. The product thus purified is isolated by lyophilization.

The lyophilizate is extracted with 2 l of absolute ethanol, contracted with acetone and then dried under vacuum at 30° C. for 18 h.

The absence of ungrafted polyethylene glycol is monitored by gel permeation chromatography, with refractometric detection.

[SH]: 0.247 mmol/g of dry product, i.e. 4.5 mol % of substitution of the amino acids.

[PEG]: 0.8 mol % substitution of the amino acids, degree recalculated according to the amount of OH-proline assayed in the modified product/unmodified product.

Example 8

Solubility of the Modified Collagenic Peptides 250 mg of the collagenic peptide are placed in 5 g of water for injection and are stirred in a sealed flask for 15 min at 40° C. The pH measurements are carried out at 30° C. The pH adjustments are carried out using 1N NaOH. A number of solubility examples are given in Table 1.

TABLE 1

| COLLAGENIC PEPTIDE OBTAINED | INITIAL APPEARANCE | SOLUBILITY |
| --- | --- | --- |
| Example 1 | pH 2.1 clear solution | no region of insolubility for a pH ranging from 2.5 to 10 |
| Example 3 | pH 2.2 clear solution | no region of insolubility for a pH ranging from 2.5 to 10 |
| Example 5 | pH 1.9 clear solution | no region of insolubility for a pH ranging from 2.5 to 10 |
| Example 7 | pH 2.5 transparent gel | gradual fluidization as the pH is increased. Fluid solution at and above pH 6 |

Example 9

Crosslinking of the Collagenic Peptides (2nd Subfamily) by Oxidation: Formation of Gels (3rd Subfamily)

The process used is the same irrespective of the collagenic peptide used (Examples 1, 3 and 7).

250 mg of lyophilizate are placed in 4.5 ml of 10 mM pH 7.4 phosphate-buffered saline (PBS) and the mixture is stirred in a sealed flask at 40° C. for 15 minutes. The pH is adjusted to 7.4±0.1 with 1N NaOH and the amount of PBS required to obtain a final collagenic peptide concentration of 50 g/l is added. The samples are placed at 37° C. 100 µl of a 1% $H_2O_2$ solution in PBS preheated to 37° C. are added to 900 µl of the collagenic peptide solution. The indications of Table 2 show that the crosslinking by oxidation (kinetics and degree), under given conditions, depends on the modified collagenic peptide used.

TABLE 2

| COLLAGENIC PEPTIDE OBTAINED | SETTING TIME OF THE GEL (37° C.) | DESCRIPTION OF THE GEL (37° C.) |
|---|---|---|
| Example 1 | 20 seconds | soft transparent homogeneous gel |
| Example 3 | 5–10 seconds | turbid homogeneous gel |
| Example 7 | 1 minute 15 seconds | soft and sticky transparent homogeneous gel |

Example 10

Crosslinking of the Collagenic Peptides by Oxidation: Formation of Films

The process for preparing the film is identical irrespective of the collagenic peptide used.

Step 1:
A solution containing 20 g/l of precursor collagenic peptide is prepared by dissolving lyophilizate in sterile water. In this example, 2.0 g of lyophilizate are dissolved in 98 g of sterile water. The mixture is stirred in a sealed container at 40° C. for 15 min in order to obtain complete dissolution. The pH of the solution is adjusted to 6.5 with 1N sodium hydroxide solution, at 25° C. The solution is stirred again at 40° C. for 10 min.

Step 2:
The solution at 40° C. is filtered through membranes of porosity 0.45 µm and then membranes of porosity 0.2 µm. The final filtration is carried out over sterile molds (polystyrene Petri dishes may be used).

Step 3:
40.0 g of filtered solution are run into two 12×12 cm² molds. The molds are closed.

Step 4:
The solution is matured, which is reflected by a physical gelation, for 24 h at a temperature of 16° C.±1° C. This temperature is necessarily less than the gel/sol transition temperature. The maturation is carried out in a chamber at controlled temperature, and the molds rest on a horizontal plate.

Step 5:
After 24 h, the mold covers are removed and the gelled solutions are evaporated over 24 h, at the same temperature in a confined chamber, in the presence of desiccants (typically sodium hydroxide pellets). After 24 h, the films obtained are dry, clear and smooth.

Step 6:
The dry films are crosslinked at 20° C., by adding 30 g of 0.3% hydrogen peroxide solution in an aqueous decimolar solution of ammonium acetate.

Step 7:
The crosslinked film is removed and washed successively with 30 g of pH 7.4 phosphate buffer and 30 g of water. All the solutions used are sterile.

Step 8:
The film is then left to dry under a laminar flow fume cupboard for 24 h. The dried films obtained contain a residual percentage of water of about 10%.

The films obtained are stable at room temperature. They remain stable and manipulable after 24 h in water or in a phosphate buffer.

Example 11

Tensile Mechanical Properties of the Films Obtained According to Example 10

The measurements of the mechanical properties of the films are carried out using a universal testing machine of DY34 type of the brand Adamel Lhomargy. The films are hydrated at ambient temperature in a phosphate buffered saline (PBS, pH=7.4) for 2 h. Next, they are cut into 4 mm by 30 mm strips using a very sharp sample punch. The thickness is measured on the hydrated samples. The samples are mounted on a cardboard frame which helps to position them in the jaws. The sample of film is kept hydrated. The frame is cut just before the tensile test, which proceeds at a constant speed of 2 mm/min. The initial modulus and the breaking stress are calculated from the tensile curves using the sections of hydrated test pieces.

The tensile properties of the films obtained according to the process described in Example 10 depend on the modified collagenic peptide used, as shown in Table 3.

TABLE 3

| COLLAGENIC PEPTIDE OBTAINED | DRY THICKNESS (µM) | WET THICKNESS (µM) | FMAX (N) | ELONGATION (%) | σ max (Mpa) | INITIAL MODULUS (MPa) |
|---|---|---|---|---|---|---|
| Example 1 | 45 | 153 | 2.9 | 43 | 3.2 | 4.6 |
| Example 2 | 45 | 94.5 | 3.1 | 28.5 | 8.1 | 21.6 |
| Example 3 | 45 | 80 | 5.4 | 42.5 | 16.7 | 25.8 |

LEGEND:
Fmax = maximum force at break
σ max = maximum breaking stress

We claim:
1. A modified collagenic peptide comprising grafted free or substituted thiol functions borne by mercaptoamino residues, wherein:
   the mercaptoamino residues are identical to or different than each other and are exclusively grafted onto the aspartic acids and glutamic acids of the collagenic chain via amide bonds, and
   said collagenic peptide is soluble in aqueous media and/or in polar solvents.
2. A constituent of implants, prostheses, dressings, artificial tissues, a bioencapsulation system, a biocompatibilizing coating, suture threads, adhesives or surgical cements, or a cell culture support, comprising the collagenic peptide according to claim 1.
3. The collagenic peptide according to claim 1, comprising grafts G different from the mercaptoamino residues and attached to at least a fraction of the free amine moieties of the collagenic chain, via amide bonds, G being an acyl group comprising a hydrocarbon-based species.
4. The collagenic peptide according to claim 3, wherein the hydrocarbon-based species comprises hetero atoms.
5. The collagenic peptide according to claim 3, wherein the hydrocarbon-based species is an alkyl and/or alkenyl and/or alicyclic and/or aromatic group.

6. The collagenic peptide according to claim 3, wherein the hydrocarbon-based species is a group comprising an optionally unsaturated alkyl chain, containing from 1 to 22 carbon(s) or a group corresponding to the formula (III) below:

Formula (III)

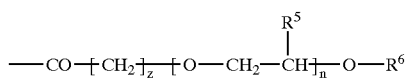

in which $R^5$ is H or $CH_3$;

$R^6$ is H or a linear or branched alkyl radical;

z is 0, 1 or 2, and n is greater than 0 and is chosen such that the molecular weight of the polymer chain is between 100 and 15,000.

7. The collagenic peptide according to claim 1, wherein at least a fraction of the mercaptoamino residues, exclusively grafted onto the carboxylic acids of the aspartic acids and glutamic acids, correspond to formula (I):

Formula (I)

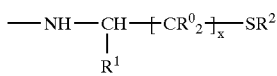

in which x=1 or 2;

$R^0$=H or $CH_3$;

$R^1$ represents H or $COOR^3$ with $R^3$ corresponding to an aliphatic, aromatic or alicyclic radical; and $R^2$ is an aliphatic and/or alicyclic and/or aromatic radical.

8. The collagenic peptide according to claim 7, wherein $R^3$ is a hydrocarbon-based radical selected from the group consisting of alkyl, alkenyl, aryl, aralkyl, alkylaryl and alkenylaryl.

9. The collagenic peptide according to claim 7, wherein $R^3$ is a hydrocarbon-based radical selected from the group consisting of methyl and ethyl.

10. The collagenic peptide according to claim 7, wherein $R^2$ is an alkyl or an acyl group.

11. The collagenic peptide according to claim 7, wherein $R^2$ is sulfurated and/or aminated.

12. The collagenic peptide according to claim 7, wherein $R^2$ corresponds to formula (II) below:

Formula (II)

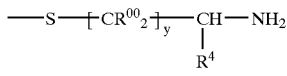

in which y=1 or 2;

$R^{00}$=H or $CH_3$; and $R^4$ represents H or $COOR^3$ with $R^3$ corresponding to an aliphatic, aromatic or alicyclic radical.

13. The collagenic peptide according to claim 7, wherein the grafted mercaptoamino residues are chosen from the group consisting of:

Formula (I.1)

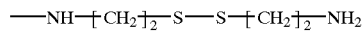

Formula (I.2)

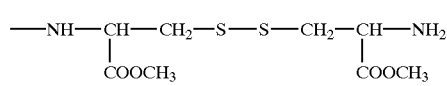

Formula (I.3)

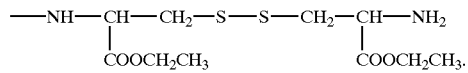

14. The collagenic peptide according to claim 7, comprising grafted mercaptoamino residues, exclusively onto the carboxylic acids of the aspartic acids and glutamic acids, correspond to formula (I'):

Formula (I')

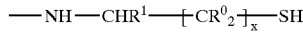

in which x=1 or 2;

$R^0$=H or $CH_3$;

$R^1$ represents H or $COOR^3$ with $R^3$ corresponding to an aliphatic, aromatic or alicyclic radical;

and being crosslinkable.

15. The collagenic peptide according to claim 14, wherein $R^3$ corresponds to an aliphatic, aromatic or alicyclic radical, hydrogen or a cation forming a salt with $COO^-$.

16. The collagenic peptide according to claim 15, wherein the cation is selected from the group consisting of $Na^+$, $K^+$ and $Li^+$.

17. A crosslinked collagenic peptide comprising collagenic chains linked together by disulfide bridges in which the constituent sulfur atoms belong to mercaptoamino residues that are exclusively grafted onto the aspartic acids and glutamic acids of the collagenic chains via amide bonds, and obtained from a crosslinkable collagenic peptide comprising grafted mercaptoamino residues, exclusively onto the carboxylic acids of the aspartic acids and glutamic acids, said collagenic peptide corresponding to formula (I'):

Formula (I')

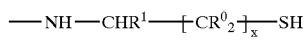

in which x=1 or 2;

$R^0$=H or $CH_3$; and $R^1$ represents H or $COOR^3$ with $R^3$ corresponding to an aliphatic, aromatic or alicyclic radical.

18. A constituent of implants, prostheses, dressings, artificial tissues, a bioencapsulation system, a biocompatibilizing coating, suture threads, adhesives or surgical cements, or a cell culture support, comprising the crosslinked collagenic peptide according to claim 17.

19. The crosslinked collagenic peptide according to claim 17, wherein in FORMULA (I') $R^3$ corresponds to an aliphatic, aromatic or alicyclic radical, hydrogen, or a cation forming a salt with $COO^-$.

20. The crosslinked collagenic peptide according to claim 19, wherein the cation is selected from the group consisting of Na$^+$, K$^+$ and Li$^+$.

21. A process for preparing a crosslinkable collagenic peptide, modified by grafting free thiol functions borne by mercaptoamino residues, said process comprising:

(a) reacting exclusively the carboxylic functions of the aspartic acids and glutamic acids of a collagenic peptide with at least one precursor of a mercaptoamino residue whose thiol function and possible carboxylic function are blocked, said reaction being done in solution and in the presence of at least one grafting agent, (b) and deprotecting the thiol function and possible carboxylic function of the mercaptoamino residues grafted onto the modified collagenic peptides obtained in step (a).

22. The process according to claim 21, comprising an additional step of functionalization with grafts G that are different from the grafts attached to the carboxylic functions of the aspartic acids and glutamic acids, this additional step of functionalization consisting essentially in carrying out an acylation of at least a fraction of the free amine functions of the collagenic chain, so as to attach thereto grafts G comprising a hydrocarbon-based species.

23. A process for preparing a crosslinked collagenic peptide from a collagenic peptide modified by grafting free thiol functions borne by mercaptoamino residues, said process comprising:

(a) reacting exclusively the carboxylic functions of the aspartic acids and glutamic acids of a collagenic peptide with at least one precursor of a mercaptoamino residue whose thiol function and possible carboxylic function are blocked, said reaction being done in solution and in the presence of at least one grafting agent;

(b) deprotecting the thiol function and possible carboxylic function of the mercaptoamino residues grafted onto the modified collagenic peptides obtained in step (a), (c) and oxidizing the thiol functions of the crosslinkable modified collagenic peptide obtained in step (b).

24. The process according to claim 23, comprising an additional step of functionalization with grafts G that are different from the grafts attached to the carboxylic functions of the aspartic acids and glutamic acids, this additional step of functionalization consisting essentially in carrying out an acylation of at least a fraction of the free amine functions of the collagenic chain, so as to attach thereto grafts G comprising a hydrocarbon-based species.

25. A process for obtaining a collagenic peptide soluble in aqueous media and/or in polar solvents and modified by grafting substituted thiol functions borne by mercaptoamino residues, comprising reacting exclusively the carboxylic functions of the aspartic acids and glutamic acids of a collagenic peptide with at least one precursor of a mercaptoamino residue in which the thiol function and the possible carboxylic function are blocked, said reaction being done in solution and in the presence of at least one grafting agent.

* * * * *